US012533287B2

(12) United States Patent
Truckai et al.

(10) Patent No.: US 12,533,287 B2
(45) Date of Patent: Jan. 27, 2026

(54) SYSTEM FOR TREATING PEYRONIES DISEASE

(71) Applicant: Kemeny Healthcare Inc., San Jose, CA (US)

(72) Inventors: Csaba Truckai, Saratoga, CA (US); Akos Toth, Cupertino, CA (US)

(73) Assignee: Kemeny Healthcare Inc., San Jose, CA (US)

( * ) Notice: Subject to any disclaimer, the term of this patent is extended or adjusted under 35 U.S.C. 154(b) by 495 days.

(21) Appl. No.: 17/303,256

(22) Filed: May 25, 2021

(65) Prior Publication Data

US 2021/0369555 A1 Dec. 2, 2021

Related U.S. Application Data

(60) Provisional application No. 63/031,459, filed on May 28, 2020.

(51) Int. Cl.

*A61H 23/00* (2006.01)
*A61B 17/22* (2006.01)
*A61H 19/00* (2006.01)

(52) U.S. Cl.

CPC ..... *A61H 23/008* (2013.01); *A61B 17/22012* (2013.01); *A61H 19/32* (2013.01); *A61B 2017/22005* (2013.01); *A61B 2017/22014* (2013.01); *A61H 2201/1207* (2013.01)

(58) Field of Classification Search

CPC .... A61B 17/225–2258; A61B 17/2251; A61H 23/008

See application file for complete search history.

(56) References Cited

U.S. PATENT DOCUMENTS 10,441,498 B1 * 10/2019 Zhu .......................... A61H 23/02
2002/0042635 A1 * 4/2002 Zhang ................ A61N 1/36007 607/39
2003/0018321 A1 * 1/2003 Rosenblum ............. A61F 5/453 604/351
2011/0040190 A1 * 2/2011 Jahnke ...................... A61B 8/12 600/459
2012/0215142 A1 * 8/2012 Spector .............. A61B 17/2251 601/46
2017/0340266 A1 * 11/2017 Gardner ................. A61K 45/00
2018/0228639 A1 * 8/2018 Hibri .......................... A61F 5/41
2018/0296383 A1 * 10/2018 Blanche ................. A61H 19/44
2019/0209431 A1 * 7/2019 Warlick ............... A61H 39/007
2019/0350803 A1 * 11/2019 Warlick .................... A61B 8/13
2020/0093857 A1 * 3/2020 Morganstern ........ A61K 31/522
2023/0218757 A1 * 7/2023 Ichim ................... C12N 5/0656 604/22

FOREIGN PATENT DOCUMENTS

CN 206526146 U * 9/2017
WO WO-2007149103 A2 * 12/2007 ............. A61B 17/22
WO WO-2012116038 A2 * 8/2012 ............... A61H 1/00

OTHER PUBLICATIONS

Wessells, H., Vacuum Erection Devices, 2006, Humana Press., Male Sexual Function. Current Clinical Urology (Year: 2006).*

* cited by examiner

*Primary Examiner* — Michael J Carey
*Assistant Examiner* — Marjan Saboktakin
(74) *Attorney, Agent, or Firm* — Levine Bagade Han LLP

(57) ABSTRACT

Systems and methods for treatment using acoustic shock waves within an enclosed negative pressure chamber to fragment or otherwise to modify plaque in a patient's penile shaft.

11 Claims, 3 Drawing Sheets

SYSTEM FOR TREATING PEYRONIES DISEASE

RELATED APPLICATION

This application is a non-provisional of U.S. Provisional No. 63/031,459 filed on May 28, 2020, the entirety of which is incorporated by reference.

FIELD OF THE INVENTION

The present invention relates to systems and methods for treating Peyronie's disease and, more particularly, to systems for generating acoustic shock waves within an enclosed negative pressure chamber to fragment or otherwise modify plaque in a patient's penile shaft. The system also may be used for treating erectile dysfunction.

BACKGROUND OF THE INVENTION

High intensity acoustic waves are known in the art for imparting mechanical forces to soft tissues in patients for treating acute and chronic conditions. Shock waves, as used in medical therapies, consist of intense pressure pulses that can be transmitted through any elastic media, such as human tissue. Acoustic shock waves are well known in urology, where such high intensity pressure pulses are adapted for fragmenting kidney stones. Shock wave therapy is also known in the field of treating erectile dysfunction (ED) where shock waves have been shown to be effective by increasing the arterial blood flow and stimulate revascularization within the two corpora cavernosa. The delivery of such acoustic energy also can fragment or soften scar tissue, and thereby enhance repair processes in soft tissues. Shock waves are characterized by instant changes in pressure when delivered to soft tissue, together with high amplitude and non-periodicity. Such shock waves can be created by various mechanisms such as electromagnets, compressed air, or electrical energy adapted to create vacuum bubbles in fluids.

Several mechanisms of action have been described for high intensity acoustic waves in soft tissue. In one aspect, acoustic waves can initiate and maintain tissue repair processes in aging or damaged tissues resulting from enhanced expression of growth factors such as the VEGF, PCNS, BMP etc. following delivery of such acoustic energy. As a result of these processes, blood vessels may be stimulated to grow which in turn can improve blood supply and oxygenation of the treated tissue. In another aspect, acoustic waves can treat plaque in blood vessels to improve blood flow in a patient's vasculature. In another aspect, shockwaves may cause the dissolution of calcified fibroblasts in some tissues. Acoustic waves may break up such existing calcifications which then can be removed by the lymphatic system.

SUMMARY OF THE INVENTION

The present disclosure includes methods and devices for the treatment of Peyronie's disease. For example, one variation of a method can include positioning at least one acoustic emitter in close proximity to a plaque in a penile shaft; disposing the penile shaft and at least one acoustic emitter in an interior chamber of a device; causing negative pressure in the interior chamber for an interval sufficient to increase blood inflow to thereby distend a corporal sinusoid; and applying shock waves from the at least one acoustic emitter to the plaque in the penile shaft.

A variation of the method can further include a negative pressure that ranges from 50 mm Hg to 250 mm Hg. Another variation of the method can include applying shock waves over a selected interval at a frequency of 1 to 5 Hz with an energy intensity of 0.10 mJ/mm2 to 0.30 mJ/mm2. The selected interval can range from 1 minute to 30 minutes. 5.

In an additional variation, the method of treating Peyronie's disease can include a selected interval, frequency and energy that are delivered in a series of treatments over time. It is believed that the shock waves modify the plaque. In additional variations, applying shock waves can be preceded by or contemporaneous with tensioning the penile shaft to thereby tension the plaque.

BRIEF DESCRIPTIONS OF THE DRAWINGS

The present invention will be more fully appreciated and understood from the following detailed description of the present invention when viewed in conjunction with the accompanying figures, in which:

FIG. 1 is a perspective view of a shockwave system adapted for treatment of Peyronie's disease by fragmenting and softening plaque in a patient's penile shaft, wherein the system includes a tubular member with an interior vacuum chamber and a component carrying a plurality of acoustic emitters that can be positioned around the penile shaft together with a woven trap that can be used to tension the penile shaft.

DETAILED DESCRIPTION OF THE INVENTION

The following detailed description describes currently contemplated modes of carrying out the invention. The description is not limiting but is made for the purpose of illustrating the general principles of the invention.

Figure 1:
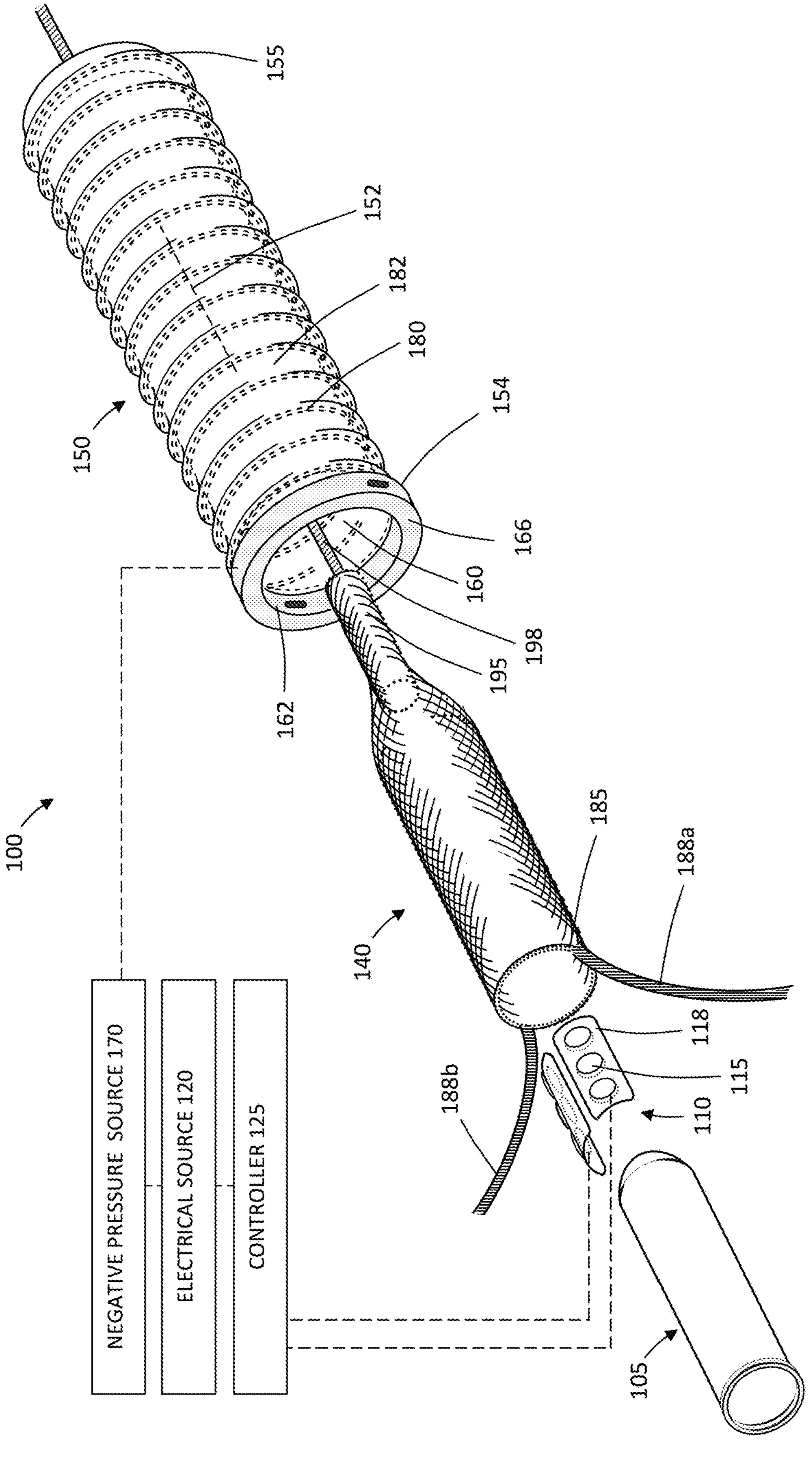

FIG. 1 illustrates a shock wave system 100 that includes several components that when assembled allow for focusing shock waves treatment on the targeted region and plaques in a subject's penile shaft.

Figure 2A:
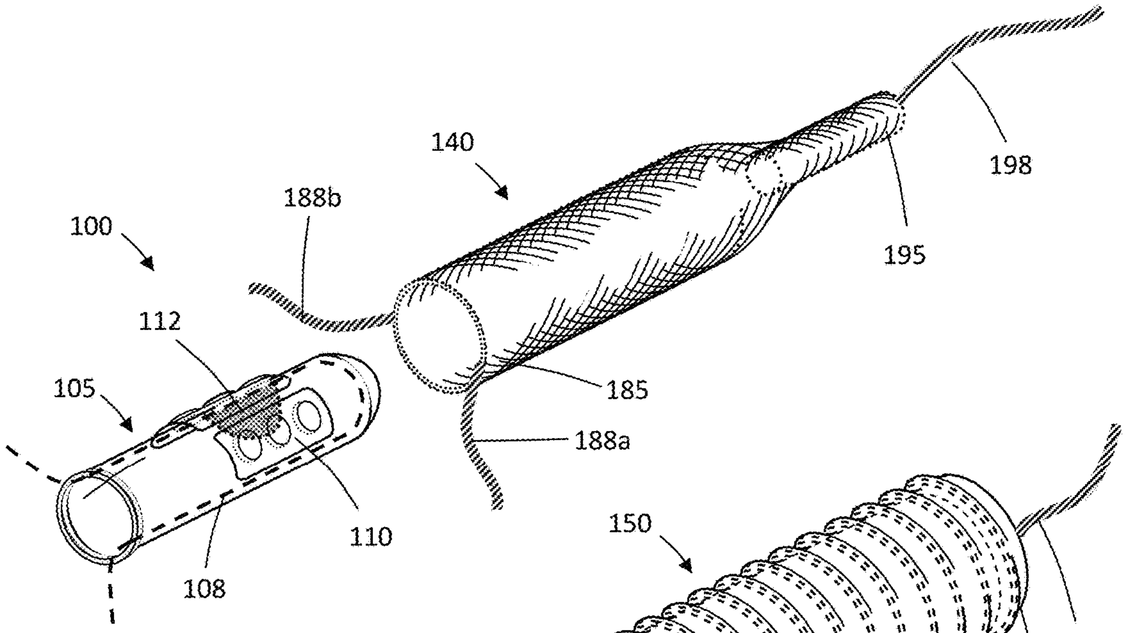
FIG. 2A illustrates the components of the system of FIG. 1 in a first step of a method of the invention wherein the subject's penile shaft is positioned in a condom or sheath and acoustic emitters in a flexible substrate are placed over the targeted region of the penile shaft.

The first component of the invention comprises a thin-wall elastomeric sheath 105 that can be similar to a condom and can be rolled on to a penile shaft 108 (see FIG. 2A). A second component of the invention comprises at least one acoustic emitter assembly 110 that is adapted for positioning on the surface of the sheath 105 overlying the targeted plaque 112. Each such emitter assembly 110 can carry one or more shockwave elements 115 which comprise a stacked piezoelectric element as will be described further below. In FIG. 1, there are two acoustic emitter assemblies 110 with each such emitter assembly shown with three piezoelectric elements 115. The piezoelectric elements 115 are carried on a flexible substrate 118 in one variation that can have an adhesive backing for coupling to the sheath 105. As can be seen in FIG. 1, the piezoelectric elements are coupled to an electrical source 120 and a controller 125 for controlling the operating parameters of the piezoelectric elements 115.

Still referring to FIG. 1, a third component of the invention comprises a mechanism for tensioning and stretching the penile shaft 108 together with and the plaque 112 (see FIG. 2A) that is targeted for treatment with shock waves. In the schematic view of FIG. 1, a cylindrical axially extendable braided structure or woven or trap 140, sometimes called as a Chinese finger toy, is provided to engage, grip and tension the penile shaft 108. Such a woven trap 140 comprises a woven structure of resilient, somewhat stiff flexible filaments that can expand in diameter when axially compressed and can contract in diameter when axially stretched. As can be understood in FIG. 1, the penile shaft 108 and sheath 105 can be inserted into the woven trap 140 (FIGS. 2A-2B) which then can be positioned in a vacuum device described next.

Referring again to FIG. 1, a fourth component of the system is an elongated tubular member 150 that is adapted to receive the subject's penile shaft 108 together with the acoustic emitters 110 and the woven trap 140. FIG. 1 further shows that the tubular member 150 extends about central or longitudinal axis 152 from a proximal end 154 to a closed distal end 155. The interior chamber 160 has an opening 162 in the proximal end 154 of the tubular member 150 which is dimensioned to receive and accommodate a flaccid or erect penile shaft 108 of a subject. A sponge-like cuff or resilient element 166 is typically provided around the proximal opening 162 of the interior chamber 160.

In this variation, referring to FIG. 1, a negative pressure source 170 is provided for evacuating air from the interior chamber 160. The negative pressure source 170 can be remote from the tubular member 150 and coupled to the device through tubing. Alternatively, a pump (not shown) can be disposed in a distal portion of the tubular member 150. The negative pressure source 170 is controlled by the controller 125. In the variation shown in FIG. 1, the tubular member 150 comprises a helical metal or plastic structure 180 combined with a flexible polymer layer 182 that allows for bending of the tubular member 150 in any direction. The helical structure 180 can comprise a malleable material that can be deformed and that will self-maintain in a deformed position. Alternatively, the helical structure 180 can consist of a spring material that returns to a straight condition. Thus, the combination of the helical structure 180 and the flexible layer 182 provides an interior chamber 160 that can hold a vacuum and not collapse inwardly.

As also can be seen in FIG. 1, the proximal end 185 of the woven trap 140 has at least one tether element and is shown with two tether elements 188*a* and 188*b* that are configured to extend through or around the proximal end 154 of the tubular member 150 to thereby maintain the position of the proximal end 185 of the woven trap 140 relative to the tubular member 150. The distal end 195 of the woven trap 140 is coupled to a distal tether 198 that is adapted to extend through the distal end 155 of the tubular member 150. A seal (not shown) is provided in the distal end 155 of the tubular member 150 to receive the tether 198 and to maintain negative pressure in the interior chamber 160. As can be understood in FIGS. 2B-2C, the penile shaft 108 then can be engaged with the woven trap 140 and axially stretched in the distal direction by pulling the distal tether 198 in the distal direction.

Typically, the tubular member 150 can be bent or deflected manually by the physician prior to receiving the patients penile shaft. Additionally, the tubular member 150 while engaging the penile shaft 108 can be straightened from a bent shape to a straighter shape to tension the targeted plaque 112 while delivering shock waves.

Figure 2B:
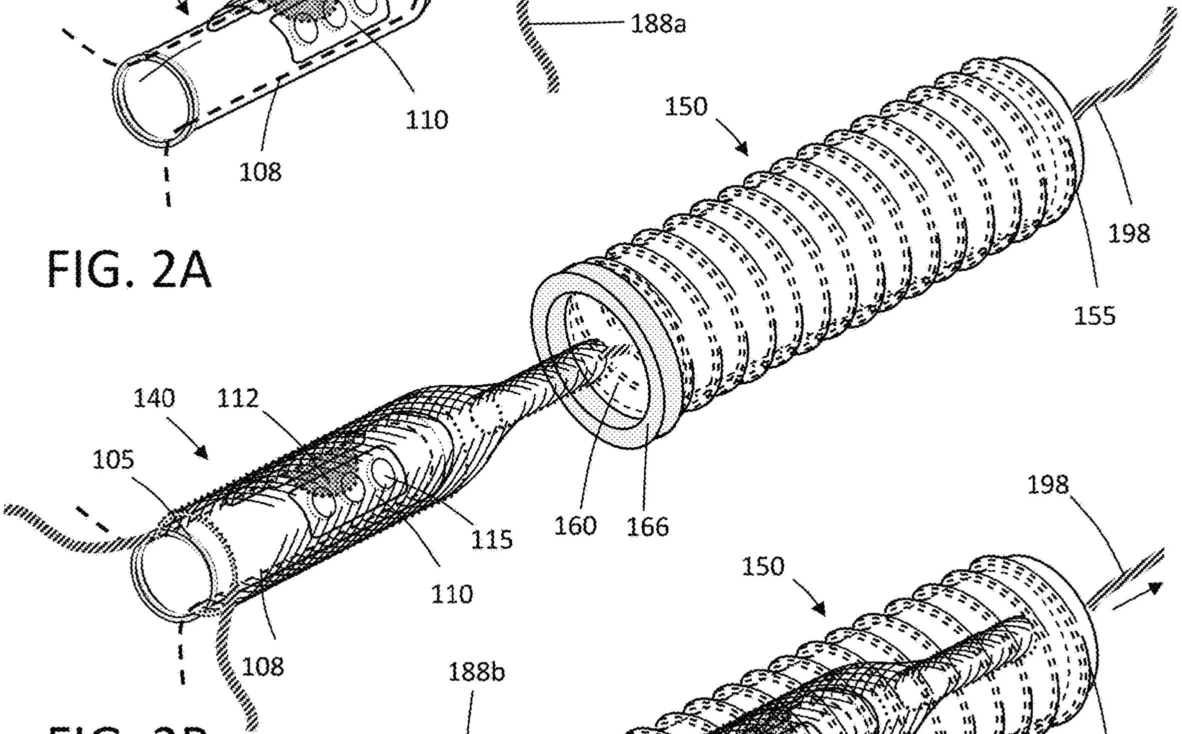
FIG. 2B illustrates another step in a method of the invention wherein the penile shaft is positioned inside the tubular woven trap.
Figure 2C:
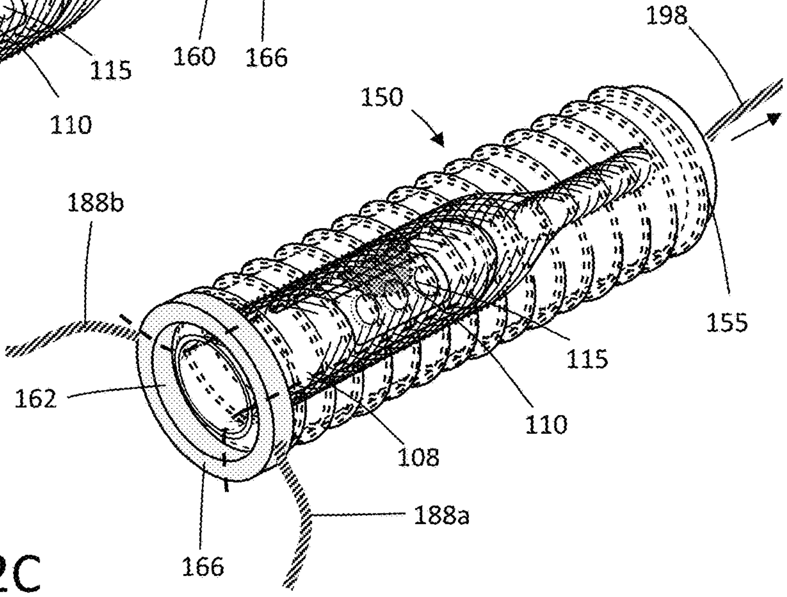
FIG. 2C illustrates a subsequent step of the method wherein the penile shaft and woven trap are positioned inside an elongated vacuum chamber and negative pressure is applied followed by energy deliver from the acoustic emitters.

Now referring to FIGS. 2A-2C, a method of the invention is shown. In FIG. 2A, the patient rolls the condom or sheath 105 over the penile shaft Next, still referring to FIG. 2A, the physician positions the acoustic or shock wave emitters 110 over the targeted region of the plaque 112. FIG. 2B then shows the assembly of the penile shaft 108, the sheath 105 and the acoustic emitters 110 inserted into the woven trap 140.

Initially, the elongated tubular member 105 may be in a straight shape or can be bent to a shape that corresponds to the curved, repose shape of a subjects penile shaft 108. FIG. 2B then shows the distal tether 198 being introduced through the interior chamber 160 of the tubular member 105 and the seal in a distal end 155 of the tubular member 150.

FIG. 2C then shows the tubular member 150 positioned over the penile shaft 108 and the emitter assembly 110. The proximal end 154 of the tubular member 150 and the sponge-like cuff or resilient element 166 around the opening 162 is pressed against the patient's body to create a closed space within the interior chamber 160. The proximal tethers 188*a* and 188*b* are secured so as to maintain the woven trap 140 in the desired position. Thereafter, the distal tether 198 can be move distally to thereby tension the penile shaft 108.

In a subsequent step of the method, the negative pressure source 170 is actuated to create negative pressure in the interior chamber 160. The air in the interior chamber 160 is evacuated by the negative pressure source 170 which will cause blood flow into the corporal sinusoids or corpus cavernosa of the penile shaft 108 to create an erect shaft in the interior chamber 160.

Thereafter, the controller is actuated to apply shock waves to the penile shaft through the plurality of piezoelectric elements 115. The acoustic emitters can be activated in unison or in sweet a sequence of the plurality of emitters. In general, a method of treating Peyronie's disease comprises positioning a patient's penile shaft in an interior chamber of a device, causing negative pressure in the chamber around the penile shaft for an interval sufficient to increase blood inflow to thereby distend the corporal sinusoids, and applying shock waves from a plurality of the piezoelectric emitters 115 to plaque 112 in the penile shaft 108. In the method, the negative pressure is from 50 mm Hg to 250 mm Hg. The method applies shock waves over a selected time interval at a frequency of 1 to 5 Hz with an energy intensity of 0.10 $mJ/mm^2$ to 0.30 $mJ/mm^2$. The selected interval can be from 1 minute to 30 minutes and can be repeated over time. A treatment session can consist of the application of from 500 to 5,000 shockwaves. The method further comprises disposing the penile shaft in the interior chamber with distended corporal sinusoids but an otherwise non-tensioned shape. The method further comprised tensioning the penile shaft to thereby tension the plaque, where the tension can be caused by straightening or lengthening the penile shaft.

Figure 3A:
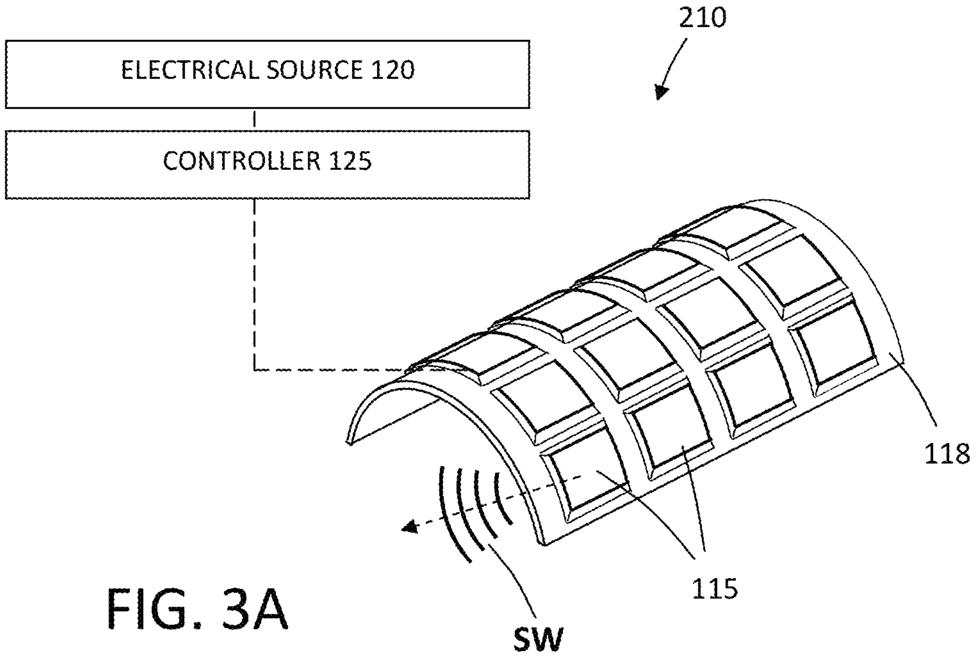
FIG. 3A is a perspective view of a shockwave applicator that includes a plurality of piezoelectric emitters disposed on a flexible substrate.
Figure 3B:
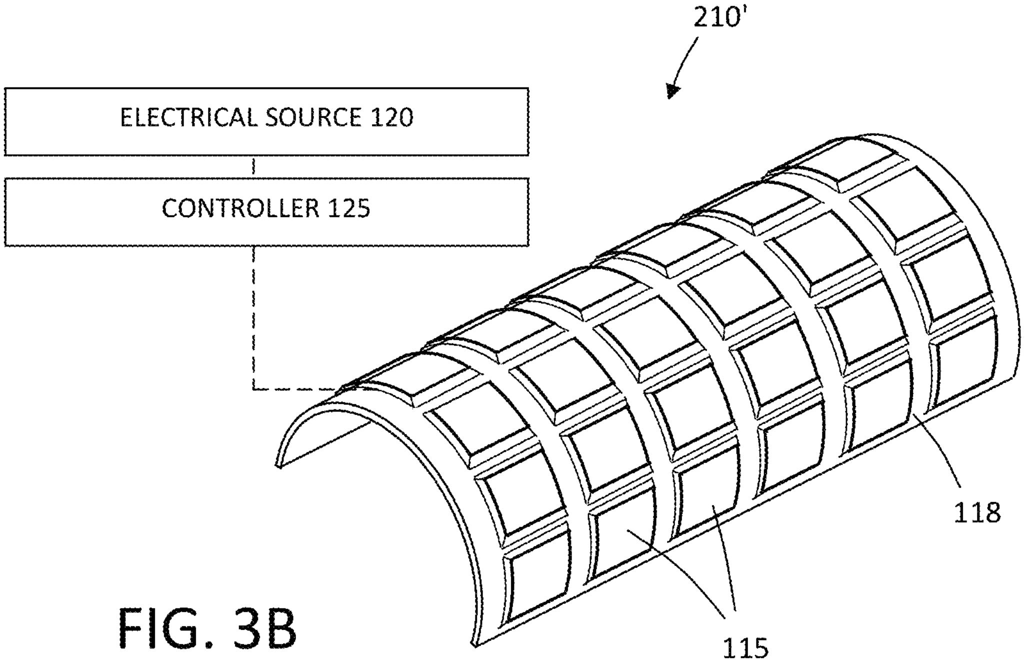
FIG. 3B is a perspective view of another shockwave applicator that is similar to that of FIG. 3A.

Now turning to FIG. 3A, an enlarged view of an exemplary acoustic emitter assembly 210 is shown that is similar to that of FIG. 1. In this variation, a plurality of individual piezoelectric elements 115 are carried on a flexible substrate 118. FIG. 3A shows for example, 16 piezoelectric elements 115. The typical piezoelectric element consists of a stack of piezoelectric layers that are adapted to increase the amplitude of the displacement of surfaces of the piezoelectric material to cause shock waves SW that are emitted orthogonal to the surface of piezoelectric material. FIG. 3B shows another emitter assembly 210' similar to that of FIG. 3A with a greater number of stacked piezoelectric emitters 115.

In other variations, it should be appreciated that light energy mechanisms, electrical stimulus mechanisms, vibration mechanisms, cooling elements such as Peltier elements, and heating elements can be provided in the interior chamber of the treatment device to enhance treatment.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise dearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of treating Peyronie's disease, comprising:

disposing a penile shaft within an elastomeric sheath having at least one acoustic emitter positioned on a surface of the elastomeric sheath;

adjusting a position of the at least one acoustic emitter in close proximity to a plaque in the penile shaft;

inserting the elastomeric sheath into a braided structure, wherein the braided structure expands in diameter when axially compressed and contracts in diameter when axially stretched such that the penile shaft stretches axially when the braided structure is axially stretched, wherein a tether is coupled to the braided structure at a distal end of the braided structure, wherein the tether is configured to be pulled distally to stretch the braided structure axially;

positioning the penile shaft, the elastomeric sheath and the at least one acoustic emitter in an interior chamber of a device via an opening in a proximal end of the device, wherein a distal end of the device is closed;

causing negative pressure in the interior chamber for an interval sufficient to increase blood inflow to thereby distend a corporal sinusoid; and applying shock waves from the at least one acoustic emitter to the plaque in the penile shaft.

2. The method of treating Peyronie's disease of claim 1 wherein the negative pressure is from 50 mm Hg to 250 mm Hg.

3. The method of treating Peyronie's disease of claim 1 wherein applying shock comprises applying shock waves over a selected interval at a frequency of 1 to 5 Hz with an energy intensity of 0.10 mJ/mm2 to 0.30 mJ/mm2.

4. The method of treating Peyronie's disease of claim 3 wherein the selected interval is from 1 minute to 30 minutes.

5. The method of treating Peyronie's disease of claim 4 wherein the selected interval, frequency and energy are delivered in a series of treatments over time.

6. The method of treating Peyronie's disease of claim 1 wherein the shock waves modify the plaque.

7. The method of treating Peyronie's disease of claim 1 wherein applying shock waves is preceded by or contemporaneous with tensioning the penile shaft to thereby tension the plaque.

8. The method of treating Peyronie's disease of claim 1 further comprising inserting the elastomeric sheath and the braided structure into the interior chamber of the device.

9. The method of treating Peyronie's disease of claim 1 wherein the device comprises a helical structure.

10. The method of treating Peyronie's disease of claim 9 wherein the helical structure comprises a spring material.

11. The method of treating Peyronie's disease of claim 1 wherein the device is a tubular member configured to bend.

* * * * *